United States Patent [19]

Butts et al.

[11] Patent Number: 4,684,244

[45] Date of Patent: Aug. 4, 1987

[54] METHOD OF SCANNING OPTICAL DENSITY PATTERNS

[75] Inventors: Gene A. Butts, Beaumont; Henry A. Garsee, Kountze; Charles D. Kelley; Bruce R. Petty, both of Beaumont, all of Tex.; James L. Pauley, Salt Lake City, Utah

[73] Assignee: Helena Laboratories Corporation, Beaumont, Tex.

[21] Appl. No.: 771,936

[22] Filed: Sep. 3, 1985

[51] Int. Cl.$^4$ .............................................. G01N 33/48
[52] U.S. Cl. ...................................... 356/39; 356/440
[58] Field of Search .................. 356/39, 344, 436, 440

[56] References Cited

FOREIGN PATENT DOCUMENTS

0195139 11/1983 Japan ..................................... 356/39

Primary Examiner—Eugene R. LaRoche
Assistant Examiner—Robert J. Pascal
Attorney, Agent, or Firm—Cullen, Sloman, Cantor, Grauer, Scott & Rutherford

[57] ABSTRACT

A method of optically scanning a plurality of optical density patterns, such as blood samples or the like is provided wherein the samples are arranged in rows and each include a plurality of optical density segments extending along a first axis, and wherein the segments generally form columns of like segments along a second axis. The optical densities of a row of segments are first scanned along the first axis, following which the centerlines of each segment in the scanned row is determined along the first axis. Then, the segments of each column are scanned along the corresponding, previously determined centerline. The centerline of each segment is determined by displacing a scanning head relative to the sample along the first axis, measuring the optical density of each segment and correlating the magnitude of the measured optical density with the relative displacement between the head and the samples. The scanning of the segments along the centerlines is performed by displacing the scanning head relative to the samples along the second axis, measuring the optical density of each segment in the column being scanned and correlating the magnitude of the measured optical density with the relative displacement of the head and the samples. Voltages are generated which are proportional to the relative displacement between the head and samples along the first and second axes, and these voltages are converted to digital data and stored in memory for later use in the correlation process. A method is also provided for determining the location of each segment in an optical density pattern and for determining the length of the pattern.

10 Claims, 10 Drawing Figures

METHOD OF SCANNING OPTICAL DENSITY PATTERNS

TECHNICAL FIELD

The present invention broadly relates to densitometers employed for analyzing optical density patterns of blood samples or the like, of the type which provides both analog and digital outputs that are employed to provide a preliminary medical diagnosis. More particularly, the invention deals with a method for scanning a plurality of optical density patterns, each of which may be associated with a different patient using the densitometer.

BACKGROUND ART

Densitometers are well known devices which are employed to scan a sample and provide an output signal or graphical display indicative of the optical density, transmittancy, absorption or the like of the scanned sample. One well known use of the densitometer involves scanning a sample of blood which has been prepared by the electrophoresis process. Electrophoresis of blood samples isolates the various proteins in the blood, known as albumin, alpha-one globulin, alpha-two globulin, beta-globulin and gamma-globulin. The electrophoresis technique separates these proteins from each other, following which the sample is scanned by an optical density pick-up. Each of the proteins exhibits a different light absorption characteristic or pattern and the patterns are graphically displayed by the densitometer to indicate the presence and quantity of each of these proteins.

The electrical analog signals generated by the optical pick-up, when graphically displayed, exhibit a series of peaks and valleys. In the analysis of blood, the area under the optical density curve and bounded by two adjacent valleys separated by one peak, is representative of the quantity of each protein in the sample and is referred to as the sample fraction. Of primary importance is the relative percentage of each protein and the selection of these fraction boundaries, i.e., the precise location of these valleys is somewhat arbitrary and results in inaccurate analysis of the blood sample. This problem is not unique to evaluation of blood samples but is common to optical and magnetic density evaluations, and, in fact, to all evaluations of analog data.

The electrophoretic process involves applying a plurality of blood samples or other substance which is to be electrophoretically separated into constituent components, on a plate. Normally a plurality of samples, typically from different patients, are applied to a single plate using an applicator or a template. The samples are typically arranged in a column and each sample migrates into the constituent components, e.g., proteins, to form rows of optical density patterns. The constituent components of the various samples migrate substantially the same distances, depending upon the thickness of the plate, the strength of the buffer employed, the length of time of process and the voltage applied during the electrophoresis process. Consequently, the end result is a plate having a series of rows of optical density patterns corresponding to each sample (patient) with like constituent components forming columns.

The plates are scanned in a densitometer system by arranging the plates in rows and columns on a flat carrier which is in turn placed on a moveable carriage beneath the optical pick-up. Scanning is performed by moving the carriage in mutually orthogonal directions in a manner such that the columns of consitiuent components are sequentially scanned in order to generate the optical density data which is used to produce an analog graphical display in the form of a curve, as previously discussed.

In the past, it has been necessary to carefully align the plates on a carrier with reference to preselected locations so that the preprogrammed scanning path passed through the centers in each optical density component of the columns. In some cases, results were less than completely satisfactory for several reasons. In some cases, the operator may skew the position of one plate relative to the other thus offsetting the columns of pattern components. In other cases, offset may occur because the degree of pattern migration between different plates may vary as a result of differences in the thickness of the plate, the strength of the buffer used, the length of time of process and the voltage applied during electrophoresis of the sample. Consequently, not all of the pattern components are scanned along their centerlines; this may result in cross talk between adjacent pattern components and in some cases, some components may not be picked up.

In addition to the foregoing problems, previous procedures for determining the precise location of the pattern components, i.e., fraction boundary location and for determining the overall length of each pattern were also subject to improvement. In the past, fraction location was performed by digitally comparing sample-amplitudes to determine when the slope changed along the scanning path. Moreover, the previous scanning procedure sometimes resulted in overscan of the pattern length, thereby increasing overall scanning time.

SUMMARY OF THE INVENTION

According to the present invention, a method is provided for optically scanning a plurality of blood samples or the like, wherein the samples are arranged in rows and each includes a plurality of optical density segments extending along a first, i.e. segment, axis, and which form columns of like segments along an orthogonal second, i.e. sample, axis. The method includes the steps of scanning the optical densities of a sample or row of the segments along the first axis, determining the centerline of each segment of the sample along the segment axis and, then, after selecting a predetermined segment, scanning the corresponding segments of all samples along the sample axis. More specifically, the sample is moved relative to the scanning head to a preprogrammed position before the first segment along the segment axis and in line with a preprogrammed centerline of the first sample along the sample axis. The sample is then scanned by displacing the sample relative to the segments along the segment axis. Optical density data corresponding to the optical density of each of the scanned segments is then generated. Displacement data corresponding to the magnitude of the displacement of the sample along the segment axis is also generated. One of the segments is then selected which has an optical density within a preprogrammed range, e.g. the minimum and maximum values. The optical density peak of the selected segment is then correlated with the displacement data along the segment axis. The sample is then moved into alignment with the centerline of the selected segment along the segment axis and before the first sample along the sample axis. The column of like segments which includes the selected segment is then scanned along the sample axis, producing optical density data of the like segments and the corresponding displacement data.

The effect of the preceding method is to determine the centerline of the optical density components of like segments in each sample thereof so that scanning may be performed along the centerlines of the samples.

A method is also provided for determining the location of each fraction or segment in an optical density pattern and for determining the length of the pattern.

BRIEF DESCRIPTION OF THE DRAWINGS

In the drawings, which form an integral part of the specification and are to be read in conjunction therewith, and in which like reference numerals are employed to designate identical components in the various views.

DETAILED DESCRIPTION OF A PREFERRED EMBODIMENT OF THE INVENTION

Figure 1:
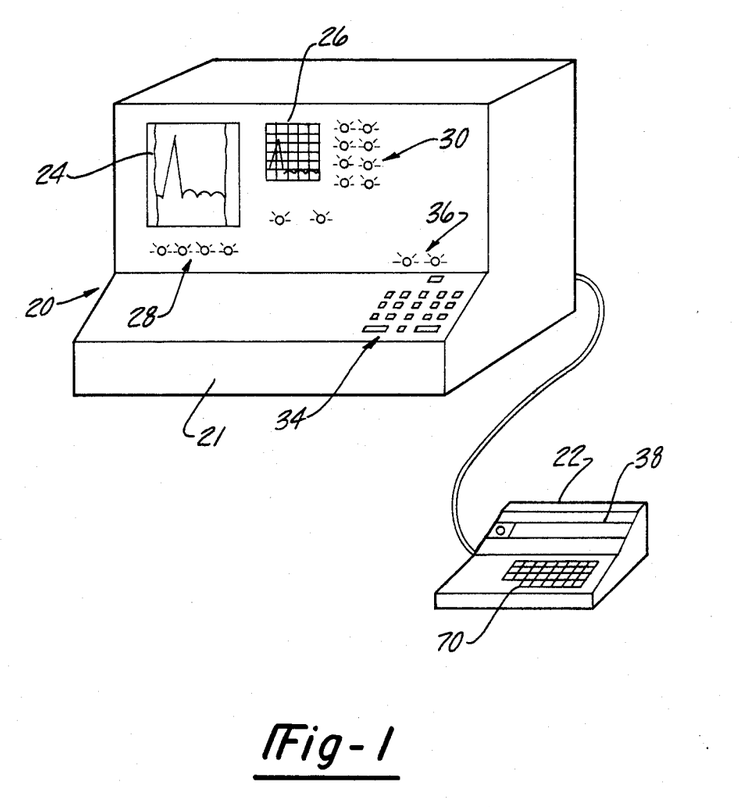
FIG. 1 is a perspective view of a diagnostic densitometer which may be employed to practice the method of the present invention.

Referring first to FIG. 1, the present invention involves a method for scanning optical density patterns using a densitometer or the like, generally indicated by the numeral 20. The densitometer 20 includes a main console 21 and an ancillary keyboard 22. The console 21 includes a printer/recorder 24 for providing a hard copy of the electrophoraragram and a clinical interpretive analysis of the scanned pattern. A CRT oscilloscope 26 provides instantaneous graphical display of the serum protein pattern or other pattern produced by the scan and is also used by the operator for manual editing of the electrophoresis pattern. A plurality of controls 30 allow positioning and editing the pattern as it is displayed on the CRT 26. Controls 32 are provided to permit selection of the filter wave length for scanning and the size of the slit used to traverse the pattern. Controls 28 may be employed by the operator to select the length of the pattern as it is printed by the printer/recorder 24, the intensity of the printout and maximum position of the printing element, as well as the position of the printing element relative to the hard copy chart paper. A pad 34 of control keys permit manual scanning and minor editing of the pattern by the operator. Controls 36 allow the operator to determine the zero or minimum point of the analog signal and the maximum gain of the analog signal.

The ancillary keyboard 22 includes a character line display 38 employing LED's or the like and a set of keys 70. The keys 70 allow major editing of the pattern, and the display 38 presents the patient sequence number, patient name and total protein count.

Figure 2:
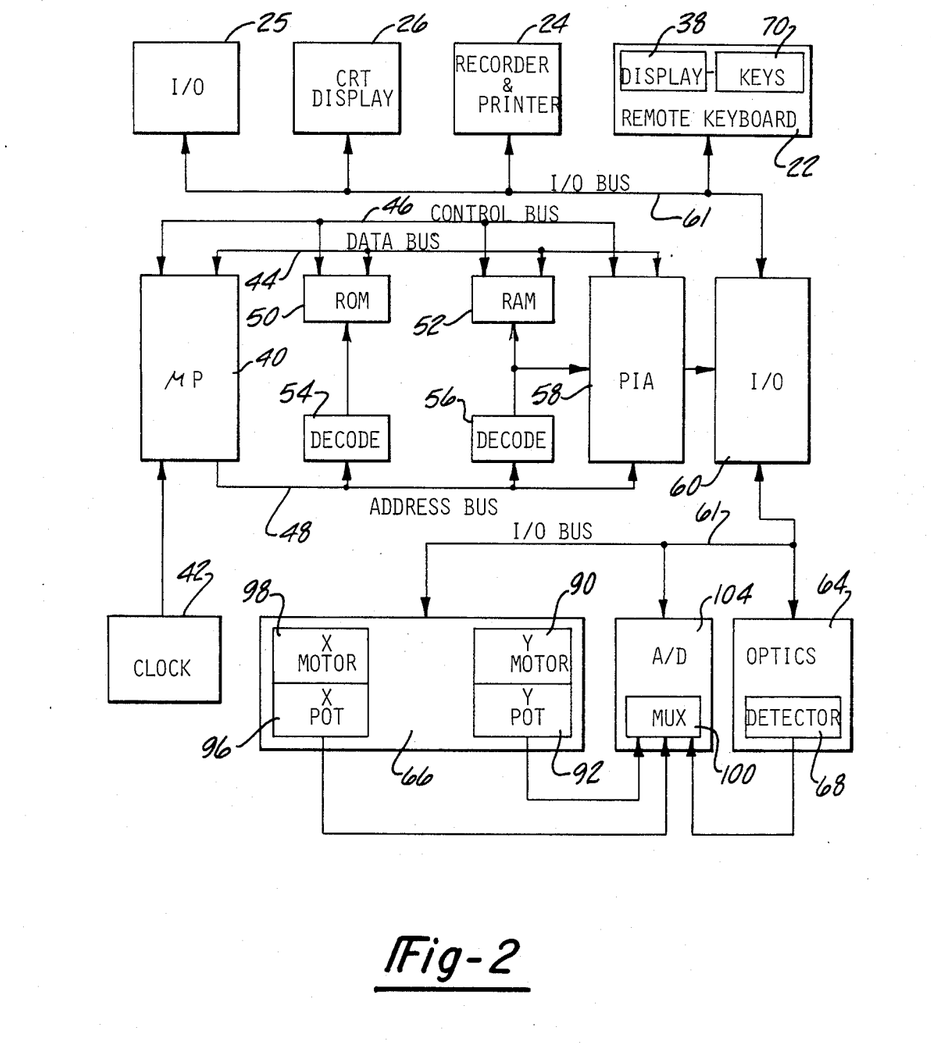
FIG. 2 is a block diagram of the circuit for the densitometer shown in FIG. 1.

Attention is now directed also to FIG. 2 which depicts, in block diagram form, one suitable circuit for the diagnostic densitometer 20, shown in FIG. 1. The system includes a microprocessor 40 that may comprise, for example a Motorola 6802 which is supplied with a time base from the clock 42. The microprocessor 40 is interconnected with a ROM 50 (read only memory), a RAM 52 (random access memory) and a PIA 58 (peripheral interface adapter). The microprocessor 40 communicates with the ROM 50, RAM 52 and the PIA 58 by means of a data bus 44 and address bus 48. Address signals delivered by the address bus 48 are decoded by decoders 54 and 56 and are employed to address memory location in the ROM 50, RAM 52 and PIA 59. Typically the address bus 48 will include 16 address lines and the data bus 44 will include 8 data lines. The control bus 46 provides control signals which selectively enable ROM 50, RAM 52 and PIA 58. The PIA 58 provides digital input/output for the microprocessor 40 and is used to interface with internal and external modules via the I/O 60 (input/output). the I/O 60 interconnects the microprocessor 40 with the remote keyboard 22, printer/recorder 24, CRT display 26 and RS232 I/O 25. The I/O 60 also interconnects the microprocessor 40 to the internal modules employed for scanning the optical density samples. These modules include the carriage 66, the A/D 104 and the optics 64.

The carriage 66 includes an X motor 98 and a Y motor 90 to move the carriage 66 in the X and Y axes and an X POT (potentiometer) 96 and a Y POT 92 to measure the X and Y axes' positional displacements.

The optics 64 includes a detector 68 to convert the optical density light signal to an electrical signal.

The A/D 104 includes a MUX 100 to allow the single A/D 104 to convert the X POT 96, Y POT 92 and detector 68 signals to digital format for use by the system.

The I/O 25 provides the interface necessary to communicate with external systems or computers.

The operating program will typically be stored in the ROM 50 while the application program will normally be stored in the RAM 52 which forms an integral part of the system, or may be loaded into the system memory from an external source such as a disk or the like. The RAM 52 will also be employed to store the database used in generating the interpretive diagnosis.

Figure 3:
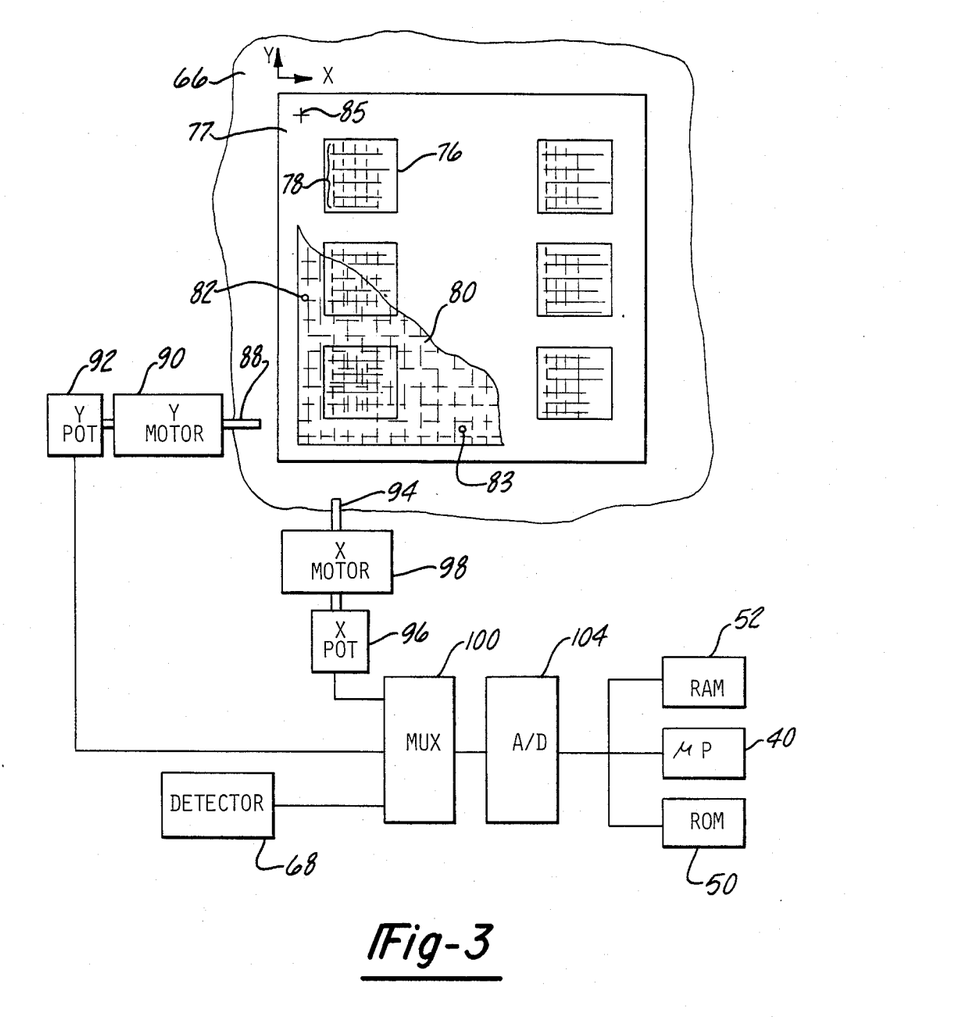
FIG. 3 is a combined plan view of a portion of the densitometer carriage having a plurality of plates mounted thereon, taken together with a block diagram of a circuit for controlling movement of the carriage.

Attention is now directed to FIG. 3, which includes a plan view of a carriage 66 which is moveable in X and Y (perpendicular) directions by a pair of DC motors 90, 98 that drive the carriage 66 via corresponding rotatable shafts 88, 94 and associated drive gear (not shown). The carriage 66 is driven in the X and Y directions relative to an optical detector head (photomultiplier tube) 68 (FIG. 2), however, it is to be understood that other types of arrangements for producing relative movement in mutually orthogonal directions between the head 68 and the carriage 66 may be provided, i.e., the carriage 66 may be stationary while the head 68 may be moveable.

A plurality of sample plates 76 are mounted in rows and columns on a flat carrier 77 which is in turn mounted in a preselected position on the carriage 66. Each of the sample plates 76 includes a plurality of serum protein patterns, collectively indicated by the numeral 78 which are produced by the electrophoresis process. Each sample pattern 78 typically corresponds to a given patient although more than one of the patterns 78 may correspond to the same patient. As will be discussed later, each of the patterns 78 includes a plurality of segments or protein fractions extending along the X axis of carriage movement which are of differing optical densities.

The sample plates 76 are placed on the carrier 77 by an operator and are aligned with each other by means of a transparent grid pattern 80 which the operator may removably mount in an indexed position on the carrier 77 by means of locating pins 82, 83, etc. After the plates 76 are aligned with each other on the carrier 77, the grid pattern 80 is removed before scanning is commenced.

As previously indicated, the carriage 66 and thus each of the sample plates 76 are driven in X and Y directions by corresponding drive motors 90 and 98. The magnitude of displacement of the carriage 66 in the X and Y directions is sensed by a pair of potentiometers 92, 96 which are driven by the output shafts 88, 94 of motors 90, 98. Potentiometers 92, 96 thus produce an analog output voltage which is proportional to the travel of the plates 76 in the X and Y directions, respectively. the analog output voltages from detector 68, Y POT 92 and X POT 96 are connected to the A/D 104 by the MUX 100. The A/D 104 digitizes these signals and, when programmed to do so, the microprocessor 40 will cause the digitized values to be stored in RAM 52. The detector 68 values represent the optical densities of the pattern and the X POT 96 values represent the X carriage positions and the Y POT 92 values represent the Y carriage positions.

It should be noted that X POT 96 and Y POT 92 (FIG. 3) are calibrated to the home position 85 so that all displacements creating changes in voltages in the potentiometers 92, 96 are with respect to the home position 85.

Figure 4:
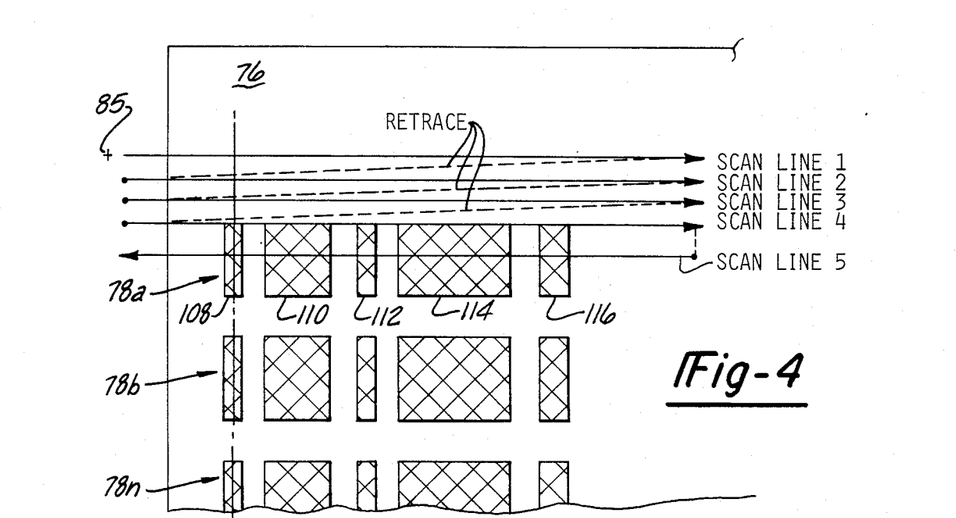
FIG. 4 is a fragmentary, enlarged view of a portion of a sample plate depicting the first step of the method for determining pattern centerline.

Referring now also to FIG. 4, the scanning process is commenced by moving the carriage 66 (FIGS. 2 and 3) such that the optical head or detector 68 moves to a home position indicated at 85 which is immediately to the left of the first fraction or segment of the pattern 78 in the X axis and on the centerline of the first pattern 78a along the Y axis. The target home position 85 is preprogrammed and stored in ROM 50, however, because of various variables, such as possible variations in the placement of the pattern 78 on the plate 76, the home position 85 may or may not, in fact, be aligned along the centerline of the Y axis of the first sample 78a.

Figure 8:
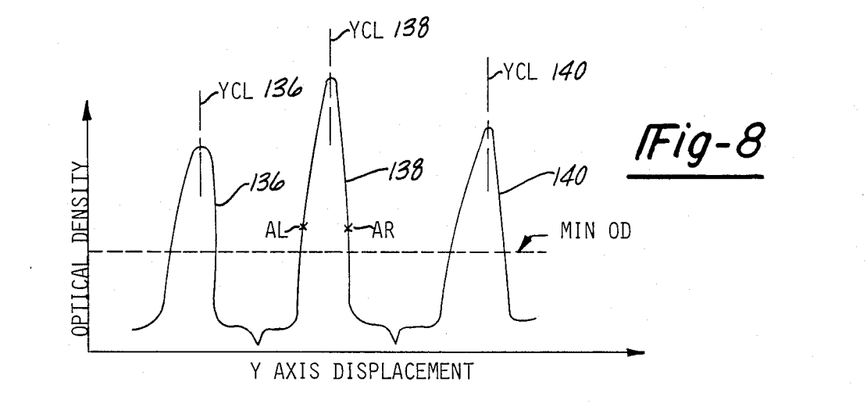
FIG. 8 is a plot of optical density versus Y axis displacement and depicting a curve resulting from the scanning step shown in FIG. 5.

As mentioned above, the scanning process is initiated by moving the carriage 66 such that the optical head 68 is positioned at home position 85; this initialization is performed under software control and is initiated by the operator actuating an appropriate key. The carriage 66 is then moved in the X direction such that the head 68 scans along the X axis to define a first scan line as indiated by Scan Line 1 in FIG. 4. The first scan line may or may not traverse one or more of the optical segments 108–116. As shown in FIG. 4, the first pattern 78a is offset from the home position 85 either because no pattern is in position 78a or the plate is positioned off the Y axis centerline as shown. Consequently, in the event that optical density segments are not encountered during the scan line, the program causes the carriage 66 to be stepped down slightly in the Y axis, whereupon a second scan is performed along Scan Line 2 along the X axis. Subsequent scans along the X axis are performed until the first optical density pattern 78a is encountered; this is indicated as Scan Line 5 in FIG. 4. The software is programmed such that the centerline of the first optical density pattern 78a is detected by searching, during the scanning process, for an optical density segment which has at least a preprogrammed minimum value MIN OD as shown in FIG. 8. For example, in scanning serum protein patterns, the search will be directed to the albumin fraction since this fraction has the highest optical density. In the event an optical density segment with an acceptable level along pattern 78a is not located within a preselected number of scans in the down direction along the Y axis, then scans are attempted in the up direction along the Y axis a like number of scans. If no pattern located in the position 78a, the software then logs the 78a position as a blank and the target position 78b is examined. This process is repeated until an acceptable pattern has been located or a distance equivalent to the maximum number of patterns has been traveled.

Figure 9:
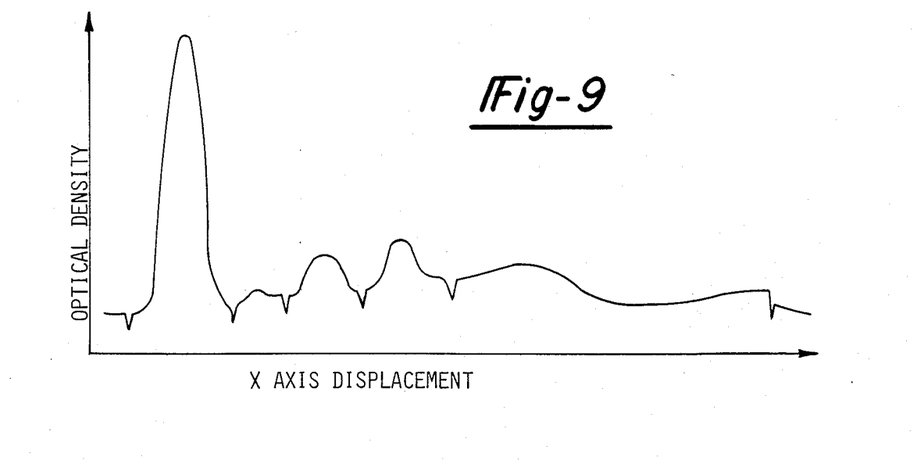
FIG. 9 is a plot of optical density versus X axis displacement showing an analog curve of the optical density of an electrophoretically prepared blood sample; and, FIG. 10 is a flow chart for a suitable computer program and method for determining the fraction location.

Assuming the preselected optical density segment is located during one of the scans along the X axis, such as Scan Line 5 (FIG. 4), the optical density of that segment, as well as the other segments in that pattern, are stored in the RAM 52. A typical pattern for serum protein is shown in FIG. 9. The microprocessor 40 then correlates the carriage positions using the digital data derived from the X POT 96 and Y POT 92 (FIG. 3) with the optical density data so that the positions of the centers of the segments 108–116 along the X axis are known.

Figure 5:
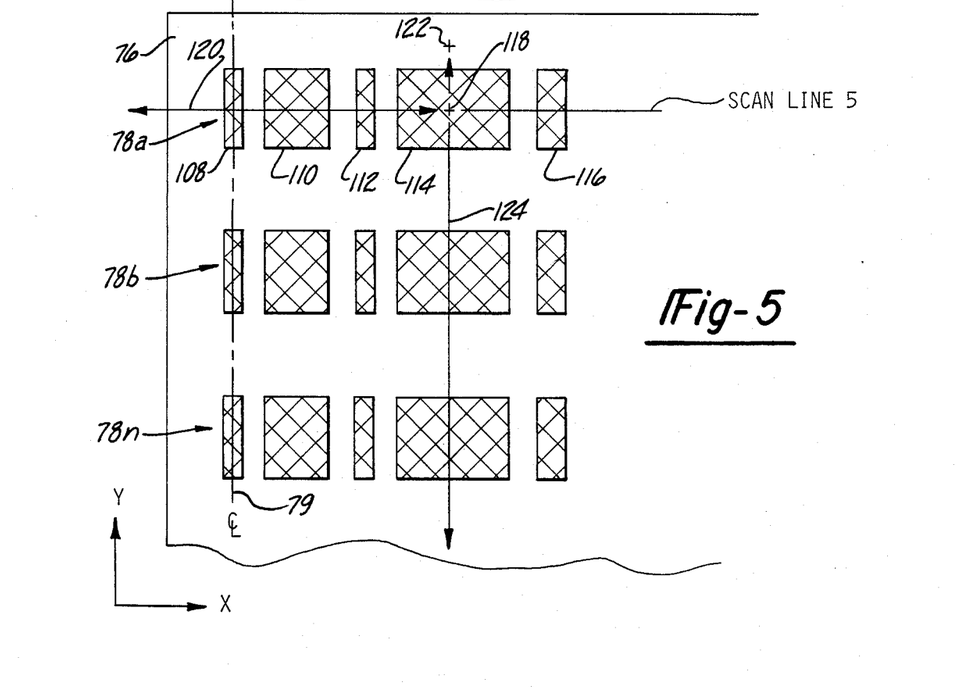
FIG. 5 is a view similar to FIG. 4 but depicting the succeeding step in the method.

Referring now to FIG. 5, the scan along the centerline of the first optical density pattern 78a is indicated by numeral 120 and the center of the selected optical segment 114 is identified by the numeral 118. The selected optical density segment 114 having been found, the carriage 66 is shifted along the X axis until the optical head 68 is aligned over the center 118 of the segment 114. The carriage 66 is displaced along the Y axis and centerline 124 until the optical head 68 is aligned at point 122 immediately above segment 114. The carriage 66 is then displaced along the Y axis such that the optical head 68 traverses a scanning path through the centers of the like segments of patterns 78a–78n which correspond to segment 114, i.e. in the case of serum protein, all of the albumin fractions would be successively scanned. Again, the optical densities of each of the scanned segments 114 are stored in RAM 52 and this data is correlated with the Y axis positions of the carriage 66 as determined by the Y POT 92 data. A typical pattern produced by this cross segment scan is shown in FIG. 8.

Figure 6:
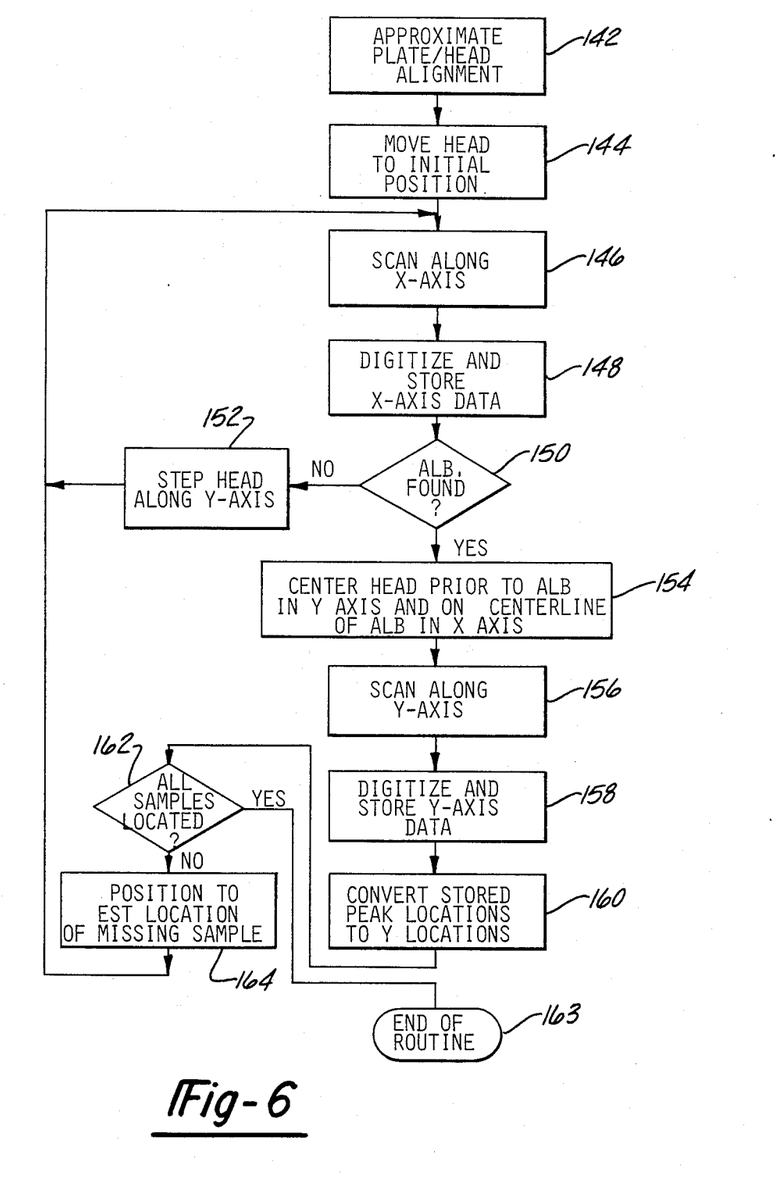
FIG. 6 is a detailed block diagram of the method and a suitable computer program for locating and scanning the centerlines of corresponding pattern segments.

A detailed flow chart of the method previously described is shown in FIG. 6 for use in scanning serum protein samples. As shown in step 142, the first step involves placing the plate 78 in an approximate preprogrammed position on the carrier 77 (FIG. 3) so that the optical density patterns are in roughly a preselected relationship or alignment to the carriage 66 and detector 68. This may be accomplished, for example, by using the template 80 (FIG. 3) previously described. The head (detector 68) or carriage 66 are then moved relative to each other in order to position the head 68 at the home position 85 (FIG. 4), as indicated at step 144. Scanning is then performed along the X axis at step 146 and the resulting optical density data corresponding to the displacement of the carriage 66 relative to the head 68 are stored at step 148. A determination is then made at step 150 whether or not the albumin albumin fraction was found; if it was not found, step 152 shows that the carriage 66 and/or head 68 are stepped slightly along the Y axis and the scanning is then repeated. If, however, the albumin is found, the head 68 is centered on the albumin fraction at 122 (FIG. 5) along X and Y axes at step 154. The albumin fractions are then scanned along the Y axis at step 156 and step 158 shows that the optical density and displacement along the Y axis are digitized and stored in RAM 52. As shown at step 160, the stored peak locations are then converted to locations along the Y axis and a determination is made at step 162 as to whether or not all samples have been located. If it is determined that all samples were located, i.e. the corresponding fractions of all samples, as shown in FIG. 8, are above a preprogrammed amplitude MIN OD then the routine is ended at step 163. However, if all samples are not located, i.e. if one or more of the corresponding fractions of all samples, as shown in FIG. 8, is below a preprogrammed amplitude MIN OD the carriage 66 and/or head 68 is positioned at the estimated position of the missing sample at step 164 and the process continues at step 146. If during this loop the missing pattern does not produce an acceptable optical density fraction (above MIN OD) the position is logged as being blank with no pattern in that position and a skip will occur when the patterns are to be scanned and drawn. This loop will continue until all patterns have been located and/or identified as blank and the end routine has been reached.

Figure 7:
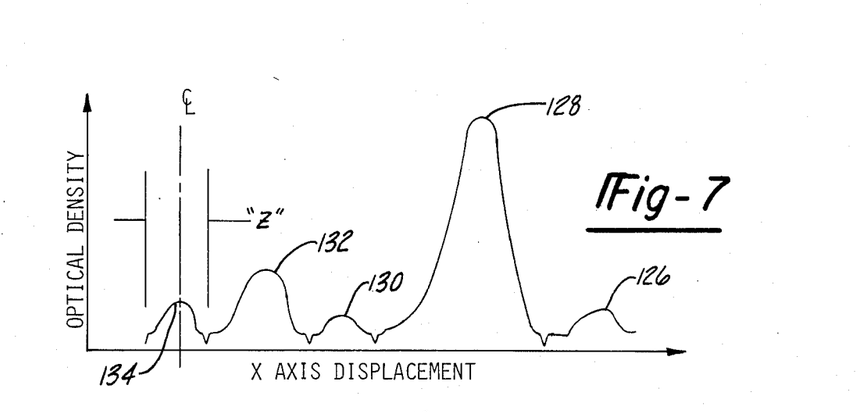
FIG. 7 is a plot of optical density versus X axis displacement and depicting the curve produced by the scanning step shown in FIG. 4.

FIG. 7 is a plot of the optical density patterns which are measured during scanning along the X axis. The peaks of the fractions 126–134 correspond to the optical density segments 116–108 shown in FIGS. 4 and 5. It is apparent that the albumin fraction 128 possesses the greatest amplitude and is therefore the fraction that is searched for during this first scanning step.

FIG. 8 depicts a plot of the optical density pattern resulting from the scan along the Y axis. The peaks of fractions 136–140 correspond, for example, to the optical density segments 114 of patterns 78a–78n. The microprocessor 40 (FIGS. 2 and 3) calculates the absolute Y axis centerline of all peaks with amplitudes greater than the preprogrammed MIN OD level as the midpoint of the two Y axis positions corresponding to equal midpoint of the two Y axis positions corresponding to equal amplitude points AL and AR located halfway between the low point and high point of each peak. AL corresponds to the equal amplitude A on the left slope and AR corresponds to the equal amplitude A on the right slope. If the optical density of any corresponding fraction is less than the preprogrammed MID OD level then the microprocessor 40 uses a preprogrammed pattern spacing to determine the target position from the last located peak, and a scan is made in the X axis to determine if a pattern is in fact in that location and has shifted because of being on a different plate or if the pattern has electrophoresed differently because of its content. If a pattern does not exist then the microprocessor 40 logs the location blank to avoid scanning and drawing blank patterns, however, if a pattern does exist then the microprocessor 40 uses the locating program depicted in the flow chart shown in FIG. 6 to locate the centerline of the offset patterns.

As previously mentioned, FIG. 9 depicts an analog curve showing typical protein fractions for a given sample. The locations of the fractions shown in FIG. 9 may be determined by an improved method according to the present invention. The method utilizes one pattern location that contains a standard that will produce a normal pattern with easily detectable peaks. The locations of the peaks determined on this standard pattern are then used as target values for the remaining patterns placed on the same plate. The target values are temporarily stored in the RAM 52 along with a predefined "window" of values that the densitometer may emloy to locate the low points near the targets within the window. This procedure normally accommodates most of the unknown patterns that may have reduced fractions that could not be located with previous techniques. It is also desirable to use target values for the unknown patterns for which, in most cases, the expected locations of fractions and the allowable window can be predefined without dedicating a pattern slot for the standard.

Figure 10:
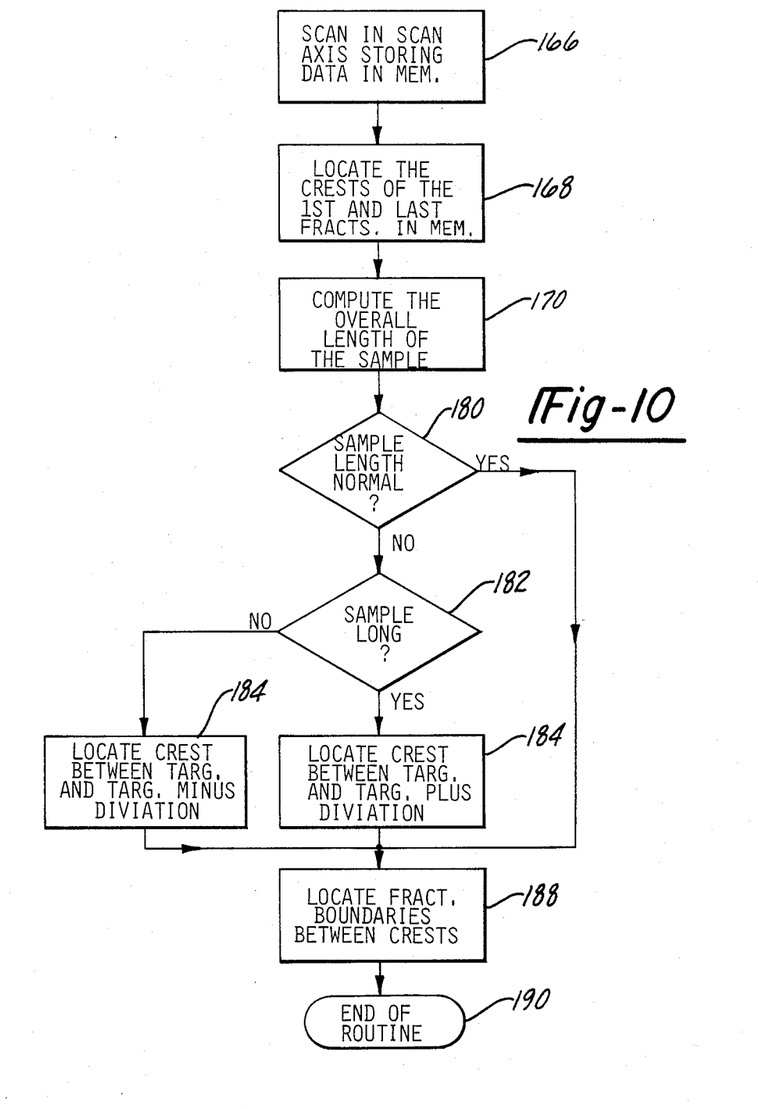

The details of this particular method are depicted in FIG. 10. The first step 166 consists of scanning along the scan (X) axis and storing the resulting optical density data in memory. Then, the crests of the first and last fractions in memory are located as shown at step 168. This last step is performed for a standard pattern. Then at step 170, a computation is made of the overall length of the sample and a determination is made at 180 as to whether the sample length is normal. If the sample length is not normal, it will be determined at 182 whether it is long. If the sample is not long, the crest between the target and the target minus allowed deviation will be located at 186 following which the fraction boundaries between the crest will be located at 188. If the sample is determined to be long as step 182, the crest between the target and the target plus allowed deviation will be located at 184. If, however, the sample length is normal, the fraction boundaries between the crests are located at 188 following which the routine is terminated at 190.

Another problem that is closely related with pattern centerline and fraction location is that of preprogrammed pattern lengths, as previously mentioned. It is highly desirable to scan the minimum distance in order speed up the scan cycle and to reduce the operator set-up time for running scans. A window approach can be applied to the final length to adjust the length, to a high, low or normal range that in turn can be used in conjunction with the method for determining fraction location in order to determine which direction to expect the fraction location to vary. If the pattern varies outside the expected range, a prompt can be used to alert the operator so that he can provide his own analysis for determining whether the cause are variations due to the operator or equipment. The multiple pattern technique used in the fraction location method can also be used in arriving at an average length of two or three patterns on the same plate without losing a pattern space for a standard.

The scanning method described above not only provides for the reliable accomplishment of the objects of the invention but does so in a particularly effective manner. It is recognized, of course, that those skilled in the art may make various modifications or additions to the preferred embodiment chosen to illustrate the invention without departing from the spirit and scope of the present contribution to the art. Accordingly, it is to be understood that the protection sought and to be afforded hereby should be deemed to extend to the subject matter claimed and all equivalents thereof fairly within the scope of the invention.

What is claimed is:

1. A method of optically scanning a plurality of blood samples or the like, said samples being arranged in rows and each including a plurality of optical density segments extendidng along a first axis, said segments generally forming columns of like segments along a second axis, comprising the steps of:
   (A) scanning the optical densities of a row of said segments along said first axis;
   (B) determining the centerline of each segment in the row scanned in step (A) along said first axis by
      displacing a scanning head relative to said samples along said first axis,
      measuring the optical density of each segment, and
      correlating the magnitude of the measured optical density with the relative displacement between said head and said samples; and
   (C) then, scanning the segments of each column along the corresponding centerline determined in step (B).

2. The method of claim 1, including the steps of generating a voltage which is proportional to the relative displacement between said head and said samples along said first axis, converting the voltage to digital data and storing said data in a memory.

3. The method of claim 1, wherein step (C) is performed by:
   displacing a scanning head relative to said samples along said second axis,
   measuring the optical density of each segment in the column being scanned, and
   correlating the magnitude of the measured optical density with the relative displacement between said head and said samples.

4. The method of claim 3, including the steps of generating a voltage which is proportional to the relative displacement between said head and said samples along said second axis, converting said voltage to digital data and storing said data in a memory.

5. The method of claim 1, wherein step (B) is performed by determining the positions of the segments along the row scanned in step (A).

6. A method of optically scanning N rows and M columns of optical density segments respectively along first and second axes, the segments in each of said rows forming an optical density pattern, comprising the steps of:
   (A) moving an optical scanning head relative to said segments and to a preprogrammed position along said first axis adjacent an end segment in one of said rows;
   (B) scanning said one row by displacing said scanning head relative to said segments along said first axis;
   (C) generating optical density data corresponding to the optical density of each segment scanned in step (B);
   (D) generating displacement data corresponding to the magnitude of displacement of said head along said first axis during step (B);
   (E) selecting one of said segments scanned in step (B) which has an optical density within a preselected range of values;
   (F) correlating the optical density data generated in step (C) with the displacement data generated in step (D);
   (G) moving said scanning head into alignment along said second axis with one with the column of optical density segments which includes the segment selected in step (E);
   (H) scanning the column of said segments which includes the segment selected in step (E);
   (I) generating optical density data correspondidng to the optical density of each segment scanned in step (H); and,
   (J) generating displacement data corresponding to the magnitude of displacement of said head along said second axis during step (H).

7. The method of claim 6, wherein steps (E), and (H) through (J) are successively repeated until all of said segments have been scanned.

8. The method of claim 6, including the step of successively moving said head relative to said segments along said second axis after completing step (B) until a segment is sensed by said head.

9. The method of claim 6, wherein said one segment selected in step (E) possesses the maximum optical density of the segments scanned in step (B).

10. The method of claim 6, wherein steps (D) and (I) are each performed by generating an analog voltage proportional to the displacement and converting said voltage to digital data.

* * * * *